(12) United States Patent
Markland et al.

(10) Patent No.: US 8,758,828 B2
(45) Date of Patent: Jun. 24, 2014

(54) PROCESS FOR PREPARING CYCLIC ESTERS COMPRISING UNSATURATED FUNCTIONAL GROUPS AND POLYESTERS PREPARED FROM SAME

(71) Applicant: Evonik Corporation, Parsippany, NJ (US)

(72) Inventors: Peter Markland, Skokie, IL (US); Xi Zhang, Columbus, OH (US)

(73) Assignee: Evonik Corporation, Parsippany, NJ (US)

( * ) Notice: Subject to any disclaimer, the term of this patent is extended or adjusted under 35 U.S.C. 154(b) by 0 days.

(21) Appl. No.: 13/768,742

(22) Filed: Feb. 15, 2013

(65) Prior Publication Data

US 2013/0171261 A1 Jul. 4, 2013

Related U.S. Application Data

(62) Division of application No. 12/968,820, filed on Dec. 15, 2010, now Pat. No. 8,399,686.

(60) Provisional application No. 61/360,148, filed on Jun. 30, 2010, provisional application No. 61/288,649, filed on Dec. 21, 2009.

(51) Int. Cl.
*A61K 9/50* (2006.01)
*C08G 63/16* (2006.01)

(52) U.S. Cl.
USPC ............................ 424/501; 528/302; 528/303

(58) Field of Classification Search
USPC .................................. 424/501; 528/302, 303
See application file for complete search history.

(56) References Cited

U.S. PATENT DOCUMENTS

| | | | |
|---|---|---|---|
| 2,668,162 | A | 2/1954 | Lowe |
| 5,288,881 | A | 2/1994 | Drysdale et al. |
| 5,496,872 | A | 3/1996 | Constancis et al. |
| 5,830,991 | A | 11/1998 | Shiiki et al. |
| 7,235,673 | B2 | 6/2007 | Yamane et al. |
| 7,538,179 | B2 | 5/2009 | Sato et al. |
| 8,399,686 | B2 * | 3/2013 | Markland et al. ............. 549/274 |
| 2006/0127786 | A1 | 6/2006 | Sugawa et al. |
| 2009/0054619 | A1 | 2/2009 | Baker et al. |

FOREIGN PATENT DOCUMENTS

| | | |
|---|---|---|
| BR | 1120120151843 | 12/2010 |
| CA | 2784995 | 12/2010 |
| CN | 2010800643260 | 12/2010 |
| EP | 10803310.1 | 12/2010 |
| HK | 13102234.7 | 2/2013 |
| IN | 5726/DELNP/2012 | 12/2000 |
| JP | 2012-546039 | 12/2010 |
| KR | 2012-7017985 | 12/2010 |
| RU | 2012131397 | 12/2010 |
| WO | 2009/127012 | 10/2009 |
| WO | WO-2009/127012 A1 | 10/2009 |
| WO | PCT/US2010/060475 | 12/2010 |

OTHER PUBLICATIONS

Jiang et al., "Clickable Polyglycolides: Tunable Synthons for Thermoresponsive Degradable Polymers," Macromolecules, 2004, 41: 1937-1944.
Radano, C.P. et al., "Synthesis of novel biodegradable copolymers using olefin metathesis," Polymer Preprints, 2002, 43(2): 727-728.
International Search Report with Written Opinion issued on Jun. 15, 2011 for Intl. Pat. App. No. PCT/US2010/060475, filed Dec. 15, 2010 (Inventor—Markland et al.; Applicant—Surmodics Pharmaceuticals, Inc.).
International Preliminary Report on Patentabilty issued on Jul. 5, 2012 for Intl. Pat. App. No. PCT/US2010/060475, filed Dec. 15, 2010 (Inventor—Markland et al.; Applicant—Surmodics Pharmaceuticals, Inc.; pp. 1-10).
Restriction Requirement issued on Jul. 23, 2012 for U.S. Appl. No. 12/968,820, filed Dec. 15, 2010 (Inventor—Markland et al.; pp. 1-9).
Response to Restriction Requirement filed on Sep. 24, 2012 for U.S. Appl. No. 12/968,820, filed Dec. 15, 2010 (Inventor—Markland et al.; pp. 1-4).
Notice of Allowance issued on Nov. 20, 2012 for U.S. Appl. No. 12/968,820, filed Dec. 15, 2010 (Inventor—Markland et al.; pp. 1-9).
Issue Notification issued on Feb. 27, 2013 for U.S. Appl. No. 12/968,820, filed Dec. 15, 2010 (Inventor—Markland et al.; pp. 1).

* cited by examiner

*Primary Examiner* — Rei-tsang Shiao
(74) *Attorney, Agent, or Firm* — Linda S. Li; Jason S. Ngui

(57) ABSTRACT

Disclosed herein are process for preparing cyclic esters comprising unsaturated functional groups. Also disclosed are copolymers prepared from the cyclic esters. The copolymers can be used to form microparticles, polymer micelles, etc., which are useful in drug delivery applications.

10 Claims, No Drawings

PROCESS FOR PREPARING CYCLIC ESTERS COMPRISING UNSATURATED FUNCTIONAL GROUPS AND POLYESTERS PREPARED FROM SAME

CROSS-REFERENCE TO RELATED APPLICATIONS

This application claims priority to U.S. application Ser. No. 12/968,820, filed on Dec. 15, 2010, which claims the benefit of U.S. Provisional Application 61/288,649, filed on Dec. 21, 2009, and U.S. Provisional Application 61/360,148, filed on Jun. 30, 2010, the entire contents of each of which are incorporated herein by reference in their entirety.

BACKGROUND

Polyesters such as poly(glycolide), poly(lactide), and poly(caprolactone) are biocompatible and biodegradable polymers that are often used in biomedical applications such as drug-delivery. Homopolymers of glycolide, lactide, or caprolactone can oftentimes be too hydrophobic in aqueous environments and can also be difficult to covalently functionalize, which limits their use for particular applications. Efforts have been made to prepare synthetic analogs of glycolide, lactide, and caprolactone in an attempt to overcome these limitations. Examples include cyclic esters having unsaturated functional groups that can react to provide modified cyclic esters or modified poly(cyclic esters) that have a desired property suitable for the application at-hand.

A method for preparing cyclic esters having unsaturated functional groups is disclosed in U.S. Patent Application Publication No. 2009/0054619 to Baker et al. According to the method, an alkynyl substituted α-hydroxy acid (alkynyl-substituted glycolide) is condensed in a dilute solution to form the cyclic ester. The resulting cyclic ester or polymer prepared from the cyclic ester can be functionalized, for example through "click chemistry," to provide a poly(cyclic ester) having a functionality tailored for a particular application. This process is limited, however, inasmuch as the reaction of the α-hydroxy acid to form the cyclic ester requires a lot of solvent and is low yielding and therefore not optimal for use in a cost-effective or industrial scale process.

Accordingly, a need exists for improved methods for preparing cyclic esters having unsaturated functional groups that overcome the aforementioned limitations. A need also exists for improved polyesters that allow for efficient functionalization that can allow for hydrophilic functional groups to be introduced onto the polymer to thereby increase the hydrophilicity of the polymer.

SUMMARY

Disclosed herein is a process for preparing a cyclic ester having the formula:

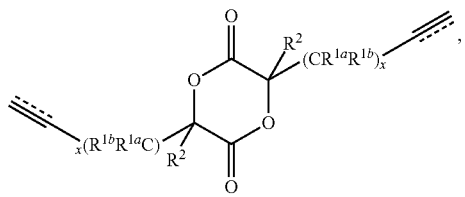

wherein each x is the same and is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; provided that each $R^{1a}$ is the same and each $R^{1b}$ is the same; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; and wherein ----- is an optional bond; the process comprising heating a liquid reaction medium comprising an oligomeric α-hydroxyacid having the formula:

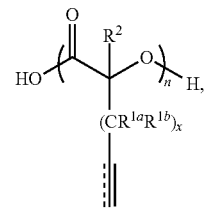

or a salt thereof, wherein n is an integer from 2 to 30, and wherein x, $R_{1a}$, $R^{1b}$, $R^2$ and ----- are the same as defined above, at a temperature of from about 150° C. to about 300° C. to form the cyclic ester, while removing from the liquid reaction medium a composition comprising the cyclic ester.

Also disclosed herein are copolymers having the formula:

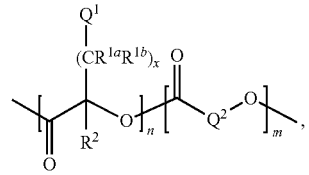

wherein n and m are each independent integers ranging from 1 to 10,000; wherein x is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $Q^1$ is —COOH or

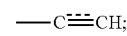

and wherein $Q^2$ is —[(CH)CH$_3$]—, —(CH$_2$)—, or —[(CH$_2$)$_5$]—.

Microparticles and micelles comprising the copolymers are also disclosed.

The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

DETAILED DESCRIPTION

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"$C_1$-$C_6$ alkyl" refers to alkyl groups having from 1 to 6 carbons, for example 1 to 4, or 1 to 3 carbons. The $C_1$-$C_6$ alkyl can be substituted or unsubstituted. Examples of $C_1$-$C_6$ alkyl groups include methyl, ethyl, propyl, isopropyl, butyl, pentyl, and hexyl. A substituted $C_1$-$C_6$ alkyl group can be substituted with 1, 2 or 3 substituents which may be the same or different. For example, the substituents can be halogen, hydroxy, or alkoxy, among others.

"$C_1$-$C_6$ alkoxy" refers to alkoxy groups having from 1 to 6 carbons, for example 1 to 4, or 1 to 3 carbons, separated by one or more oxygen atoms (i.e., an ether linkage. Examples of $C_1$-$C_6$ alkoxy groups include methoxy, ethoxy, n-propoxy, i-propoxy, n-butoxy, sec-butoxy, t-butoxy, hydroxymethoxy, 2-hydroxyethoxy and 2-hydroxypropoxy. A substituted $C_1$-$C_6$ alkoxy group can be substituted with 1, 2 or 3 substituents which may be the same or different. For example, the substituents can be halogen, hydroxy, or alkoxy, among others.

"$C_1$-$C_6$ alkylthio" refers to alkylthio groups having from 1 to 6 carbons, for example 1 to 4, or 1 to 3 carbons, separated by or terminated with one or more sulfur atoms. Examples of alkylthio groups include methylthio, ethylthio, n-propylthio, i-propylthio, n-butylthio, sec-butylthio, t-butylthio, hydroxymethylthio, 2-hydroxyethylthio and 2-hydroxypropylthio. A substituted $C_1$-$C_6$ alkylthio group can be substituted with 1, 2 or 3 substituents which may be the same or different. For example, the substituents can be halogen, hydroxy, or alkoxy, among others.

"$C_1$-$C_6$ alkylamino" refers to alkylamino groups having from 1 to 6 carbons, for example 1 to 4, or 1 to 3 carbons, separated by or terminated with one or more nitrogen atoms. Examples of alkylamino groups include methylamino, ethylamino, n-propylamino, i-propylamino, n-butylamino, sec-butylamino, t-butylamino, hydroxymethylamino, 2-hydroxyethylamino and 2-hydroxypropylamino. A substituted $C_1$-$C_6$ alkylamino group can be substituted with 1, 2 or 3 substituents which may be the same or different. For example, the substituents can be halogen, hydroxy, or alkoxy, among others.

"$C_1$-$C_6$ hydroxyalkyl" refers to alkylamino groups having from 1 to 6 carbons, for example 1 to 4, or 1 to 3 carbons, substituted with one or more hydroxyl groups. Examples hydroxyalkyl groups include hydroxymethyl, hydroxyethyl, hydroxypropyl, hydroxybutyl and hydroxyhexyl. A substituted $C_1$-$C_6$ hydroxyalkyl group can be substituted with 1, 2 or 3 substituents which may be the same or different. For example, the substituents can be halogen or alkoxy, among others.

"Salts" of the α-hydroxyacid or oligomeric α-hydroxyacid refer to carboxylate salts of the α-hydroxyacid or oligomeric α-hydroxyacid, which can include a variety of cations, such as alkali metal cations, for example sodium.

The term "microparticle," includes nanoparticles, microspheres, nanospheres, microcapsules, nanocapsules, and particles, in general. As such, the term microparticle refers to particles having a variety of internal structure and organizations including homogeneous matrices such as microspheres (and nanospheres) or heterogeneous core-shell matrices (such as microcapsules and nanocapsules), porous particles, multi-layer particles, among others. The term "microparticle" refers generally to particles that have sizes in the range of about 10 nanometers (nm) to about 2 mm (millimeters).

A "bioactive agent," refers to an agent that has biological activity. The biological agent can be used to treat, diagnose, cure, mitigate, prevent (i.e., prophylactically), ameliorate, modulate, or have an otherwise favorable effect on a disease, disorder, infection, and the like. Bioactive agents also include those substances which affect the structure or function of a subject, or a pro-drug, which becomes bioactive or more bioactive after it has been placed in a predetermined physiological environment.

The cyclic esters of the invention are prepared by a depolymerization process wherein an oligomeric α-hydroxyacid is depolymerized to form the cyclic ester. The cyclic esters can also be prepared by a two-step process wherein an oligomeric α-hydroxyacid is first prepared from the corresponding α-hydroxyacid by polymerization, followed by the depolymerization process. The two-step process can be carried out in a single reaction vessel (one-pot) or more than one reaction vessel.

In one aspect, the process of the invention comprises preparing a cyclic ester by heating a liquid reaction medium comprising an oligomeric α-hydroxyacid at a temperature effective to form the cyclic ester, preferably from about 150° C. to about 300° C., while removing from the liquid reaction medium a composition comprising the cyclic ester. The cyclic ester is formed through a depolymerization (transesterification) reaction of the oligomeric α-hydroxyacid.

During the process for converting the oligomeric α-hydroxyacid to the cyclic ester, the oligomeric α-hydroxyacid and the cyclic ester are in equilibrium. Under ambient conditions, the equilibrium is shifted toward the oligomeric α-hydroxyacid. However, under reduced pressure and/or at high temperatures, the equilibrium shifts in favor of the cyclic ester. Accordingly, the depolymerization process is carried out at an elevated temperature and/or under reduced pressure. The temperature at which the depolymerization process is carried out is at least high enough to send the formed cyclic ester into the vapor phase so that the cyclic ester can be distilled off from the liquid reaction medium. As the cyclic ester is formed, the cyclic ester is distilled off from the liquid reaction medium and collected as distillate. Preferably, the cyclic ester is distilled off while the depolymerization reaction is occurring, i.e. continuously or even simultaneously with the depolymerization reaction. Quick distillation of the cyclic ester off from the liquid reaction medium ensures that the reaction equilibrium favors the formation of the cyclic ester. To aid in the formation of the cyclic ester, a transesterification catalyst can be used in a catalytically-effective amount.

The liquid reaction medium, during the depolymerization process, is heated to a temperature of from about 150° C. to about 300° C., preferably from about 230° C. to about 300° C., and more preferably from about 230° C. to about 290° C. The depolymerization process can be carried out under atmospheric or reduced pressure. Ideally, the conditions will be such that most if not all of the oligomeric α-hydroxyacid is in the molten state and/or dissolved if the process is carried out using a solvent. Preferably, the depolymerization process is carried out under reduced pressure, i.e., less than about ambient pressure, or less than about 760 torr. In some aspects, the depolymerization process is carried out at a pressure of less than about 50 torr, for example from about 0.02 torr to about 50 torr. More preferably, the process is carried out under very high vacuum, for example from about 0.02 torr to about 1 torr. Such low pressures can allow for the easy removal, for example through distillation or sublimation, and recovery of the cyclic ester as it is formed.

The processes can be carried out with or without the use of a solvent for dissolving the oligomeric α-hydroxyacid or α-hydroxyacid. Preferably, the process is carried out solvent-free, i.e., wherein the oligomeric α-hydroxyacid is depolymerized in the liquid reaction medium that is free of solvent, i.e., in the melt, or bulk polymerized. In this instance, the oligomeric α-hydroxyacid is heated to a temperature which renders the oligomer molten, for example from about 150° C. to about 300° C. In other aspects, however, the process can be carried out using a solvent, which will typically be a polar solvent capable of substantially dissolving the oligomeric α-hydroxyacid. The solvent should be a high-boiling solvent since the process is carried out at a high temperature and/or reduced pressure. Accordingly, suitable solvents are those that have a boiling point within the range of from about 150° C. to about 450° C., and more preferably from about 230° C. to about 450° C.

Examples of such high-boiling polar solvents include alkoxyalkyl esters of aromatic carboxylic acids, alkoxyalkyl esters of aliphatic carboxylic acids, polyalkylene glycol ethers and polyalkylene glycol esters. For example, when these high-boiling polar organic solvents are used by themselves in a proportion of generally about 0.3-50 times by weight to relative to the oligomer, they are capable of dissolving the oligomer at a temperature around 230° C. at which the depolymerization of the oligomer takes place. Specific examples of these solvents include bis(alkoxyalkyl)phthalates such as di(2-methoxyethyl)phthalate, dialkylene glycol dibenzoates such as diethylene glycol dibenzoate, and polyethylene glycol ethers such as hexaethylene glycol dimethyl ether. Other specific examples of solvents include benzylbutyl phthalate, dibutyl phthalate, diamyl phthalate and dipropyl phthalate; and benzoic esters such as benzyl benzoate. Still further examples include adipic esters such as octyl adipate and sebacic esters such as dibutyl sebacate, and tricresyl phosphate.

The liquid reaction medium, prior to the depolymerization process, can also comprise impurities, whether the process is solvent-free or not. For example, a crude mixture of oligomeric α-hydroxyacids can be used and may comprise residual α-hydroxyacids left from the polymerization process used to form the oligomers.

The cyclic ester is removed from the liquid reaction medium by any suitable method such as distillation or sublimation. The distillate or solid from sublimation can also comprise other impurities, such as α-hydroxyacids or low molecular weight oligomers left over from previous process steps. Accordingly, the distillate or solid from sublimation comprising the cyclic ester can be further purified as needed, for example by washing with a non-solvent for the cyclic ester to remove impurities, by recrystallizing the cyclic ester, or even by re-distilling the cyclic ester. The cyclic ester can also be further purified by separating it from a mixture by centrifugal precipitation or decantation. The cyclic ester can be washed with a non-solvent for the cyclic ester such as cyclohexane or ether. The cyclic ester can be recrystallized using a solvent such as ethyl acetate or diethyl ether. When sublimation is used, the cyclic ester is vaporized from the liquid reaction medium and collected as a solid in a cold trap. The solid collected from sublimation can likewise comprise other impurities and can therefore be purified accordingly.

In a further aspect of the process, and prior to, continuously with, or simultaneously with the depolymerization step wherein the cyclic ester is formed, the process comprises polymerizing an α-hydroxyacid or a salt thereof by heating a liquid reaction medium comprising the α-hydroxyacid at an effective temperature, preferably from about 100° C. to about 300° C. for an effective time, preferably ranging from about 0.5 hours to about 24 hours, and preferably under vacuum, to form the oligomeric α-hydroxyacid in the liquid reaction medium and subsequently, continuously, or simultaneously performing the depolymerization step in the same or different reaction vessel to form the cyclic ester, which is then removed from the liquid reaction medium. This step is preferably carried out by melt-polymerization or bulk-polymerization, wherein no solvent is used.

According to this aspect of the process, the α-hydroxyacid can be heated at a temperature of from about 100° C. to about 250° C., preferably from about 140° C. to about 230° C., and more preferably from about 140° C. to 160° C., under reduced pressure, atmospheric pressure or sufficient pressure in the presence of an optional polymerization catalyst to conduct a condensation reaction. Preferably, this step is carried out under high vacuum. After the formation of the oligomers of the α-hydroxyacid, the oligomers can be subjected to the depolymerization process discussed above. The polymerization reaction can be carried with or without a solvent. Preferred solvents in include high boiling polar solvents such as those discussed above. The polymerization reaction is preferably carried out with little or no added solvent, i.e., in the melt or in bulk.

In some aspects, the entire process, including the formation of the oligomeric α-hydroxyacid is carried in a single reaction vessel as a one-pot process. In other aspects, the oligomeric α-hydroxyacid can be isolated and/or purified before the depolymerization process is carried out. Various purification methods for the oligomers can be used, such as precipitation, or washing with a non-solvent, such as benzene or toluene to remove unreacted α-hydroxyacid or oligomers with undesirably low molecular weights.

The polymerization and/or depolymerization steps of the process can optionally be carried out using a catalytically-effective amount of a catalyst. The polymerization and transesterification catalyst can be the same or different. The formation of the oligomeric α-hydroxyacid can be carried out with any suitable catalyst known to polymerize α-hydroxyacids. The polymerization catalyst can be metallic or non-metallic, including a variety of non-metallic organic catalysts. Suitable metal catalysts include zinc powder, tin powder, aluminum, magnesium and germanium, metal oxides such as tin oxide (II), antimony oxide (III), zinc oxide, aluminum oxide, magnesium oxide, titanium oxide (IV) and germanium oxide (IV), metal halides such as tin chloride (II), tin chloride (IV), tin bromide (II), tin bromide (IV), antimony fluoride (III), antimony fluoride (V), zinc oxide, magnesium chloride and aluminum chloride, sulfates such as tin sulfate (II), zinc sulfate and aluminum sulfate, carbonates such as magnesium carbonate and zinc carbonate, borates such as zinc borates, organic carboxylates such as tin acetate (II), tin octanoate (II), tin lactate (II), zinc acetate and aluminum acetate, organic sulfonates such as tin trifluoromethane sulfonate (II), zinc trifluoromethane sulfonate, magnesium trifluoromethane sulfonate, tin (II) methane sulfonate and tin (II) p-toluene sulfonate. Dibutyltin dilaurate (DBTL), $Sb_2O_3$, Ti(IV)bu, Ti(IV)iso, and others.

The polymerization catalyst can also be a non-metallic acids, such as an organic acid. The organic acid can be a weak acid or a strong acid. Examples of suitable organic acids include acetic acid, methane sulfonic acid, ethane sulfonic acid, 1-propane sulfonic acid, 1-butane sulfonic acid, trifluoromethane sulfonic acid, benzene sulfonic acid, p-toluene sulfonic acid, p-xylene-2-sulfonic acid, naphthalene-1-sulfonic acid and naphthalene 2-sulfonic acid, and stronger acids such as hydrochloric acid, sulfuric acid, glacial acetic acid, and phosphoric acid.

The transesterification catalyst can be any of those catalysts discussed above, and is preferably one of the metallic oxide-based catalysts such as zinc oxide. In a preferred aspect of the process, the polymerization catalyst is sulfuric acid and the transesterification catalyst is zinc oxide (ZnO).

The polymerization catalyst or transesterification catalyst can be used in catalytically-effective amounts, which will vary widely depending upon the particular reaction conditions. The optimum catalytically-effective amounts for any particular system can readily be determined through trial runs. For example, the quantity of catalyst can be such that the reaction mass contains from about 0.01 to about 10% by weight or more, and preferably from about 0.1 to about 5%, or from about 0.9 to about 5%. For the depolymerization reaction, for example, higher catalyst loadings can be desirable because oligomer residence time can decrease in some aspects with increases in the initial transesterification catalyst concentration, which can thereby speed-up the cyclic ester production rate. The same can also be true for the polymerization catalyst. When the polymerization catalyst is a non-metallic acid, the amount of the transesterification catalyst can be chosen such that the transesterification catalyst is present in an excess quantity (mole basis) to that of the polymerization catalyst.

Generally, the cyclic esters have the formula:

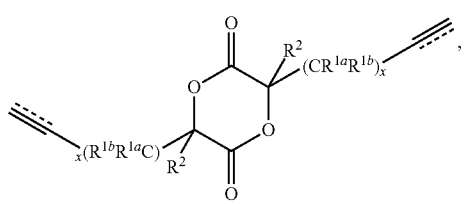

wherein each x is the same and is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; provided that each $R^{1a}$ is the same and each $R^{1b}$ is the same; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; and wherein ----- is an optional bond.

Preferred cyclic esters have the formula:

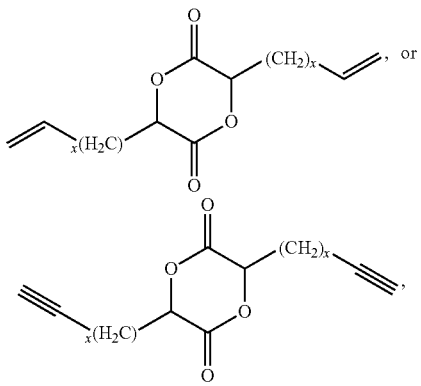

wherein x is defined above. More preferably, x is an integer from 0 to 6, and more preferably, x is an integer from 1 to 3. In specific examples, x is 1 or 2. In a specific aspect, the cyclic ester is 3,6-di(prop-2-yn-1-yl)-1,4-dioxane-2,5-dione or 3,6-diallyl-1,4-dioxane-2,5-dione.

The oligomeric α-hydroxyacid from which the cyclic ester is produced has the formula:

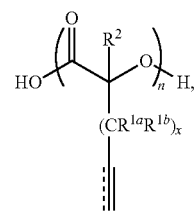

or a salt thereof, wherein n is an integer from 2 to 20, and wherein x, $R^{1a}$, $R^{1b}$, $R^2$ and ----- are the same as defined above.

Preferred oligomeric α-hydroxyacids correspond to the preferred cyclic esters discussed above, i.e., those α-hydroxyacids having the formula:

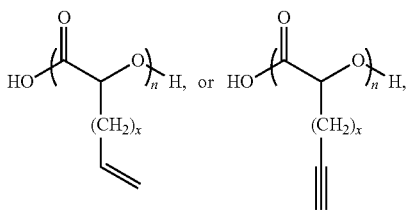

wherein x is defined above. More preferably, x is an integer from 0 to 6, and more preferably, x is an integer from 1 to 3. In specific examples, x is 1 or 2. In a specific aspect, the oligomers are oligomers of 2-hydroxy-4-pentynoic acid or 2-hydroxy-4-pentenoic acid.

The degree of polymerization (i.e., the value of n) and the resultant molecular weight of the oligomeric α-hydroxyacid, after the polymerization step, can vary widely so long as the oligomer can be made molten and depolymerized at the desired operating temperature and pressure. For example, the value of n can be from about 2 to about 30, or from about 5 to 20, and preferably from about 10 to about 15. Degrees of polymerization and molecular weights of the oligomeric α-hydroxyacid can be determined using methods known in the art, such as NMR spectroscopy or gel-permeation chromatography (GPC). When the process of the invention is carried out in a single vessel, a sample of the oligomeric α-hydroxyacid can be removed from the liquid reaction medium prior to the completion of the depolymerization reaction and analyzed to determine molecular weight or degree of polymerization.

During the depolymerization reaction, the value of n can increase as the reaction progresses such that any heel (i.e., polymeric residue) remaining upon completion of the depolymerization reaction has a greater degree of polymerization than the starting oligomeric α-hydroxyacid. In some aspects of the invention, however, the oligomeric heel recovered after depolymerization can have a sufficiently low value of n such that the heel can be recycled directly into the same or a subsequent process for converting additional quantities of the cyclic ester.

The α-hydroxyacid which is used to prepare the oligomeric α-hydroxyacid has the following formula:

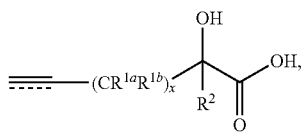

or a salt thereof, wherein x, $R^{1a}$, $R^{1b}$, $R^2$ and ----- are the same as defined above.

Preferred α-hydroxyacids have the formula:

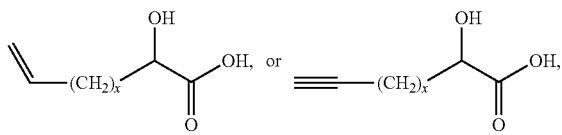

wherein x is defined above. More preferably, x is an integer from 0 to 6, and more preferably, x is an integer from 0 to 2. In specific examples, x is 0 or 1.

The α-hydroxyacid can be prepared using methods known in the art. For example, the α-hydroxyacid can be prepared according to methods disclosed in U.S. Patent Application Publication No. 2009/0054619 to Baker et al., which is incorporated herein by reference in its entirety at least for its teachings of α-hydroxyacid synthesis.

For example, the alkyne-based α-hydroxyacid can be prepared according to Scheme 1.

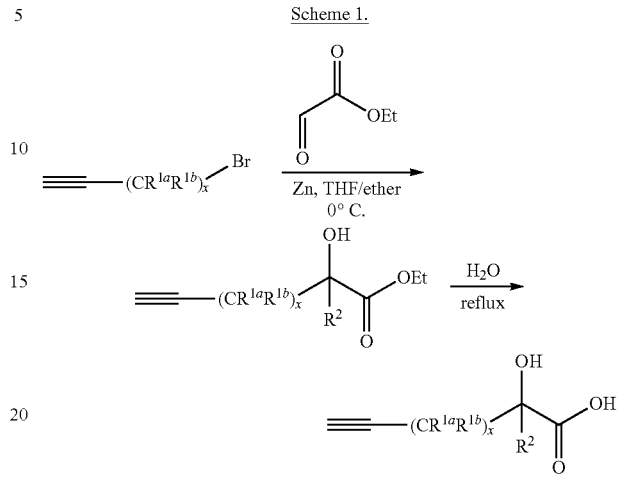

Scheme 1.

In a further aspect, the alkene-based α-hydroxyacid can be prepared according to Scheme 2.

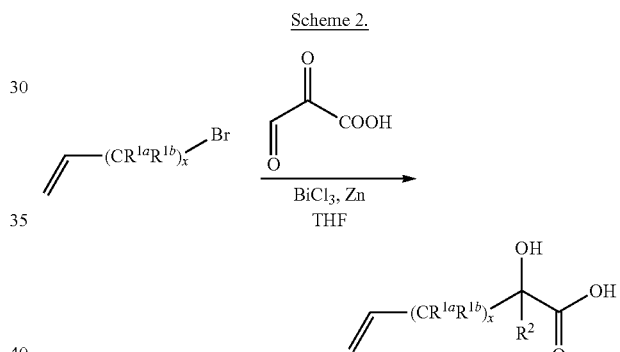

Scheme 2.

Specific examples of α-hydroxyacids from which the corresponding oligomeric α-hydroxyacids can be prepared and subsequently used to prepare the corresponding cyclic ester include without limitation 2-hydroxy-4-pentynoic acid and 2-hydroxy-4-pentenoic acid, or a carboxylate salt thereof.

The cyclic esters of the invention can be useful in a variety of applications, but are particularly desirable for use in biomedical applications such as drug delivery. Many of the polymers prepared from the cyclic esters of the invention, such as those discussed above, can be useful as pharmaceutical carriers in pharmaceutical formulations comprising bioactive agents that can be delivered to a subject.

The process described above can be used to prepare the copolymers of the invention. Generally, the copolymers have the formula:

wherein n and m are each independent integers ranging from 1 to 10,000; wherein x is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $Q^1$ is —COOH or

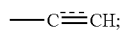

and wherein $Q^2$ is —[(CH)CH$_3$]—, —(CH$_2$)—, or —[(CH$_2$)$_5$]—.

Copolymers wherein $Q^1$ is —COOH have the general formula:

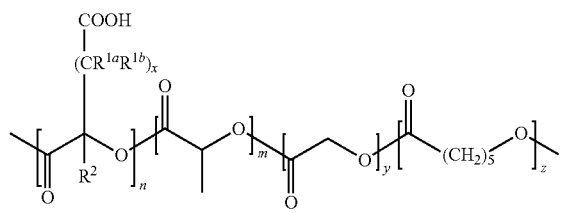

wherein n is an integer ranging from 1 to 10,000; wherein m, y, and z are each independent integers ranging from 0 to 10,000, provided that at least one of m, y, or z are greater than 0; wherein x is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl.

More specifically, copolymers wherein $Q^1$ is —COOH have the formula:

(Ia)

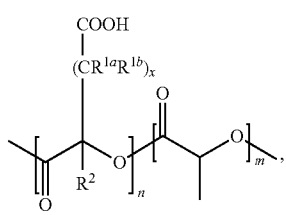

(IIa)

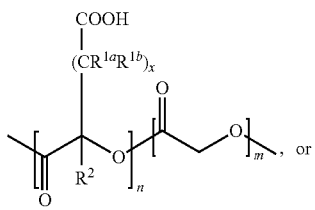

(IIIa)

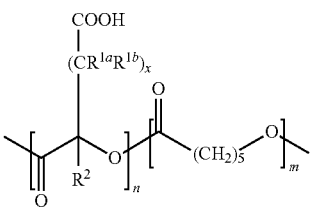

wherein n and m are each independent integers ranging from 1 to 10,000; wherein x is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; or (IVa)

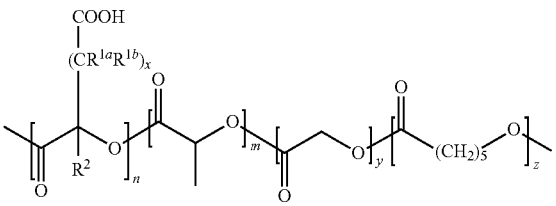

wherein n is an integer ranging from 1 to 10,000; wherein m, y, and z are each independent integers ranging from 0 to 10,000, provided that at least two of m, y, or z are greater than 0; wherein x is an integer ranging from 0 to 12; wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl; wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl.

In one aspect, x is 1. In another aspect, x is 2. In a further aspect, $R^2$ is hydrogen. In one aspect, $R^{1a}$ is hydrogen. In a further aspect, $R^{1b}$ is hydrogen. In one aspect, $R^{1a}$ and $R^{1b}$ are each hydrogen.

The copolymers of the invention can be random, block, or blocky copolymers. When the copolymers are block copolymers, any sequence of monomer units can be used. Thus, the unsaturated residue can be attached to a lactide, glycolide, or caprolactone residue in any poly(lactide), poly(glycolide), poly(caprolactone), poly(lactide-co-glycolide), poly(glycolide-co-caprolactone), or poly(lactide-co-glycolide-co-caprolactone). Copolymers including lactide, glycolide, and/or caprolactone can comprise any sequence of lactide, glycolide, and/or caprolactone along with the unsaturated monomer.

Specific non-limiting examples of the copolymers of the invention, wherein $Q^1$ is —COOH, include without limitation those having the following formulae:

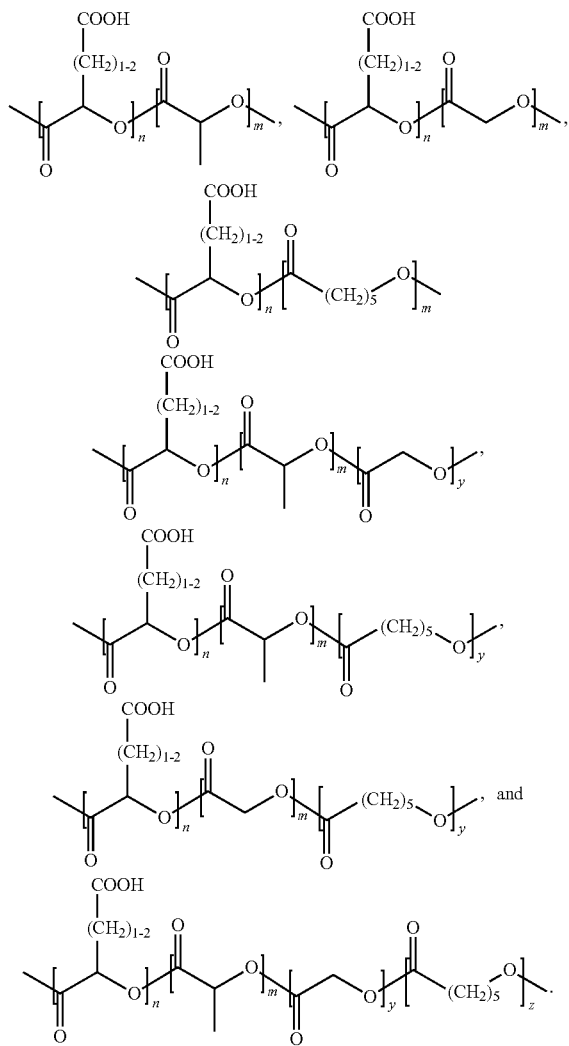

wherein, as shown, x is 1 or 2, $R^{1a}$ and $R^{1b}$ are each hydrogen, and $R^2$ is hydrogen.

The polymers of the invention can be prepared from the corresponding cyclic esters, as discussed above. Polymers of formula (I) can be prepared by copolymerizing lactide and the unsaturated cyclic ester, followed by oxidation of the unsaturated group to form the carboxylic acid on the copolymer. Polymers of formula (II) and (III) can be prepared by copolymerizing glycolide or caprolactone, respectively, along with the an unsaturated cyclic ester, followed by oxidation of the unsaturated group to form the carboxylic acid, while polymers of formula (IV) can be prepared analogously starting with lactide, glycolide, and/or caprolactone, and the unsaturated cyclic ester monomer.

Lactide, glycolide, and/or caprolactone monomers, as discussed above, can be copolymerized with the unsaturated cyclic ester to provide the copolymers of the invention, which can then be oxidized to provide the carboxylic acid containing copolymers of the invention. In some aspects, the biodegradable polymer comprises one or more lactide residues. The copolymer can comprise any lactide residue, including all racemic and stereospecific forms of lactide, including, but not limited to, L-lactide, D-lactide, and D,L-lactide, or a mixture thereof.

When poly(lactide-co-glycolide), poly(lactide), or poly(glycolide) is used, along with the unsaturated monomer, the amount of lactide and/or glycolide in the copolymer can vary. For example, the copolymer can contain 0 to 100 mole %, 40 to 100 mole %, 50 to 100 mole %, 60 to 100 mole %, 70 to 100 mole %, or 80 to 100 mole % lactide and/or from 0 to 100 mole %, 0 to 60 mole %, 10 to 40 mole %, 20 to 40 mole %, or 30 to 40 mole % glycolide, wherein the amount of each monomer present is 100 mole %.

In a further aspect, the polymer can comprise a poly(caprolactone) or a poly(lactide-co-caprolactone) or a poly(glycolide-co-caprolactone). For example, the polymer can be a poly(lactide-caprolactone), which, in various aspects, can comprise 0 to 100 mole %, 40 to 100 mole %, 50 to 100 mole %, 60 to 100 mole %, 70 to 100 mole %, or 80 to 100 mole % lactide and/or from 0 to 100 mole %, 0 to 60 mole %, 10 to 40 mole %, 20 to 40 mole %, or 30 to 40 mole % caprolactone, wherein the amount of each monomer present is 100 mole %.

The copolymerization process involving the unsaturated monomer along with lactide and/or glycolide can be carried out according to Schemes 3a-c.

Scheme 3a. Copolymers of Formula (I)

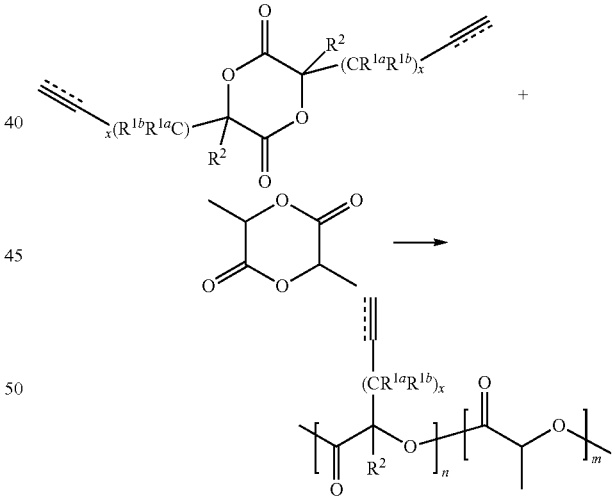

Scheme 3b. Copolymers of Formula (II)

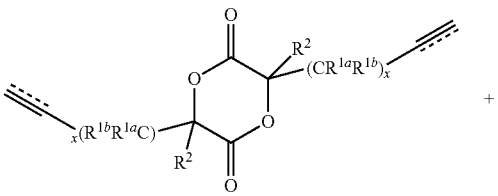

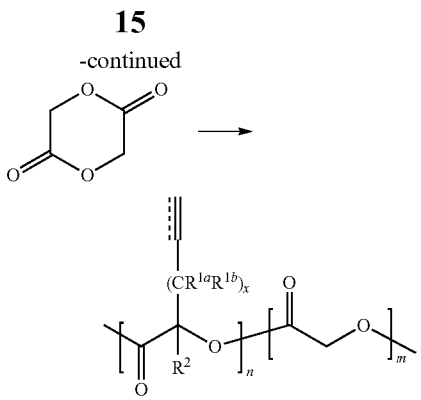

Scheme 3C. Copolymers of Formula (III)

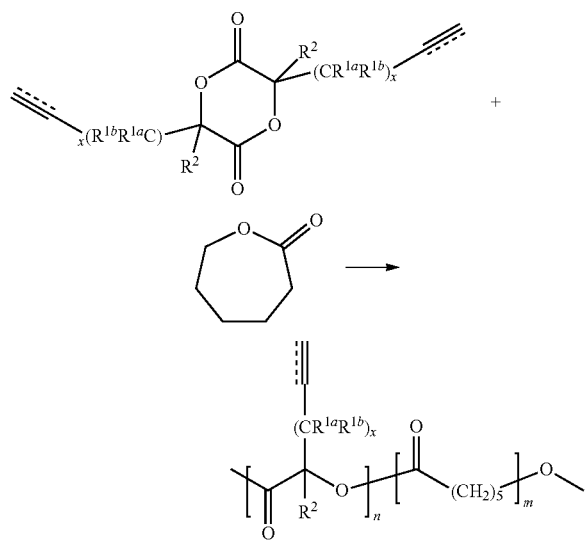

Scheme 3d. Copolymers of Formula (IV)

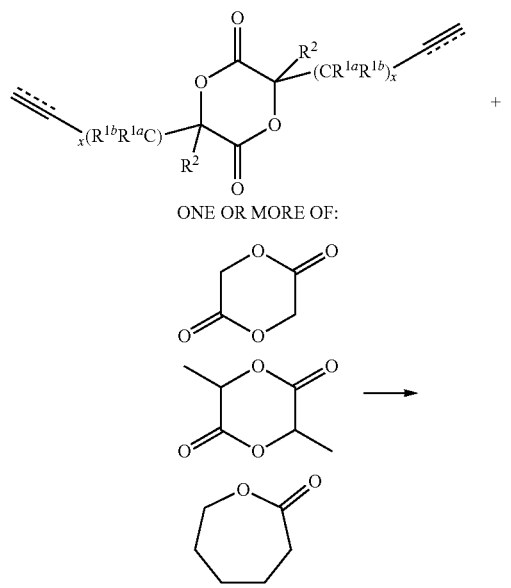

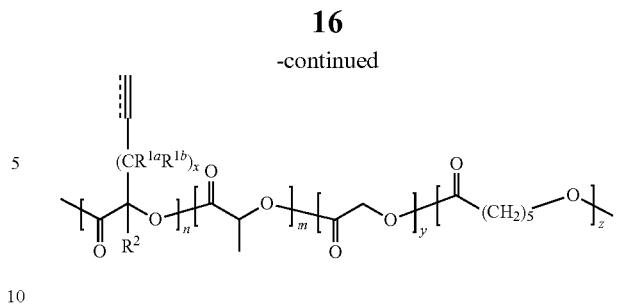

The polymerization step in forming the copolymers can be carried out using known techniques. The copolymerization can optionally be carried out using a catalytically-effective amount of a catalyst. The polymerization catalyst can be metallic or non-metallic, including a variety of non-metallic organic catalysts. Suitable metal catalysts include zinc powder, tin powder, aluminum, magnesium and germanium, metal oxides such as tin oxide (II), antimony oxide (III), zinc oxide, aluminum oxide, magnesium oxide, titanium oxide (IV) and germanium oxide (IV), metal halides such as tin chloride (II), tin chloride (IV), tin bromide (II), tin bromide (IV), antimony fluoride (III), antimony fluoride (V), zinc oxide, magnesium chloride and aluminum chloride, sulfates such as tin sulfate (II), zinc sulfate and aluminum sulfate, carbonates such as magnesium carbonate and zinc carbonate, borates such as zinc borates, organic carboxylates such as tin acetate (II), tin octanoate (II), tin lactate (II), zinc acetate and aluminum acetate, organic sulfonates such as tin trifluoromethane sulfonate (II), zinc trifluoromethane sulfonate, magnesium trifluoromethane sulfonate, tin (II) methane sulfonate and tin (II) p-toluene sulfonate. Dibutyltin dilaurate (DBTL), $Sb_2O_3$, Ti(IV)bu, Ti(IV)iso, and others.

The copolymerization catalyst can also be a non-metallic acid, such as an organic acid. The organic acid can be a weak acid or a strong acid. Examples of suitable organic acids include acetic acid, methane sulfonic acid, ethane sulfonic acid, 1-propane sulfonic acid, 1-butane sulfonic acid, trifluoromethane sulfonic acid, benzene sulfonic acid, p-toluene sulfonic acid, p-xylene-2-sulfonic acid, naphthalene-1-sulfonic acid and naphthalene 2-sulfonic acid, and stronger acids such as hydrochloric acid, sulfuric acid, glacial acetic acid, and phosphoric acid.

The copolymerization catalyst can be used in catalytically-effective amounts, which will vary widely depending upon the particular reaction conditions. The optimum catalytically-effective amounts for any particular system can readily be determined through trial runs. For example, the quantity of catalyst can be such that the reaction mass contains from about 0.01 to about 10% by weight or more, and preferably from about 0.1 to about 5%, or from about 0.9 to about 5%.

Specific examples of the unsaturated copolymers that can be prepared using the methods described above include without limitation the following copolymers.

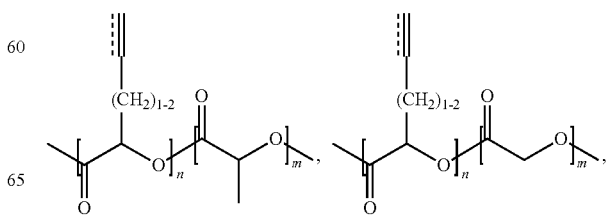

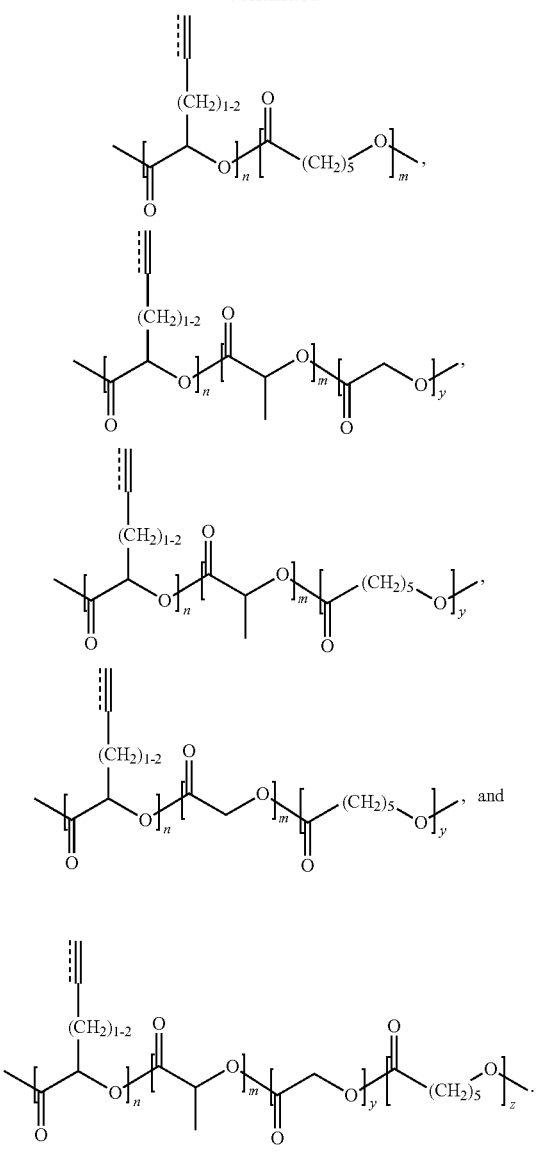
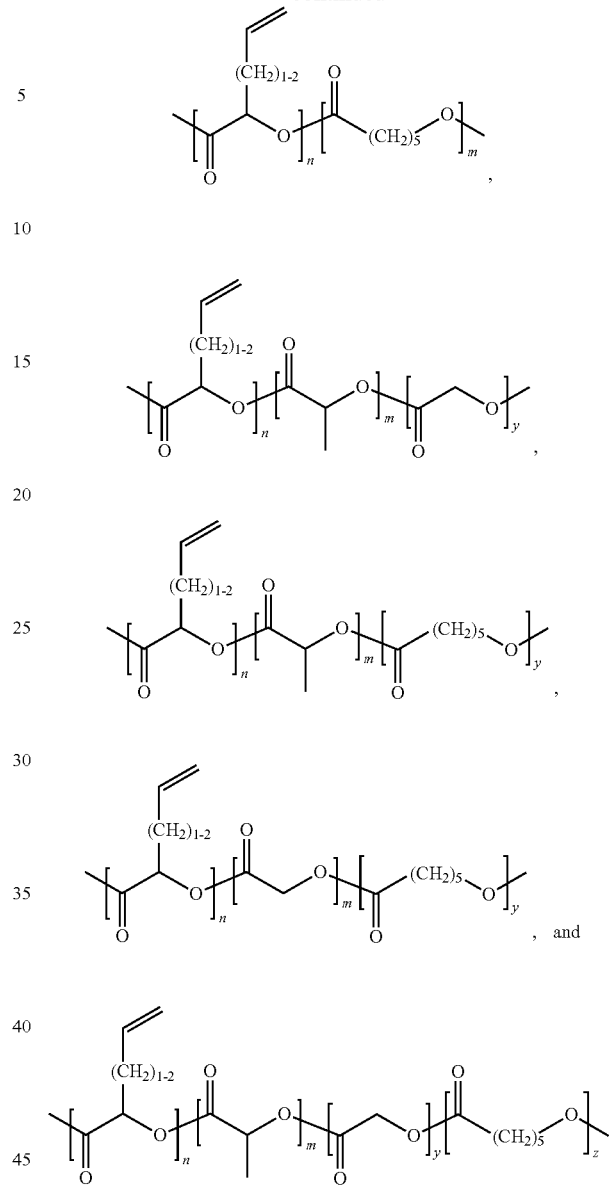

Other specific examples of the unsaturated copolymers included without limitation the following copolymers.

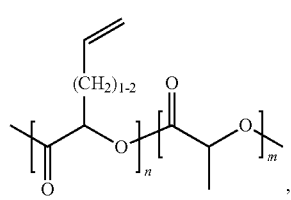

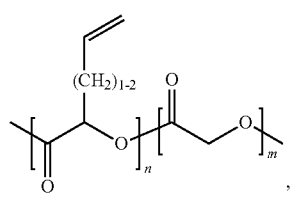

The endgroups of the copolymers of the invention can be any suitable endgroup and will generally depend on any initiator used during polymerization. For example, if water is used to initiate the copolymerization, one end group of the copolymer will be —OH and the other end group will be —H. Other initiators include a variety of alcohols, such as alkyl-alcohols, such as 1-decanol, and hydroxy-acids, which will provide alcohol or hydroxy-acid end groups. The polymerization can also be initiated with mPEG-OH to get an AB block copolymer. Likewise, the polymerization can be initiated with a diol, such as HO-PEG-OH to get an ABA block copolymer.

After forming the unsaturated copolymer, the carboxylic acid functional group can be introduced by oxidizing the unsaturated functional group with a suitable oxidizing agent, according to Scheme 4.

Scheme 4.

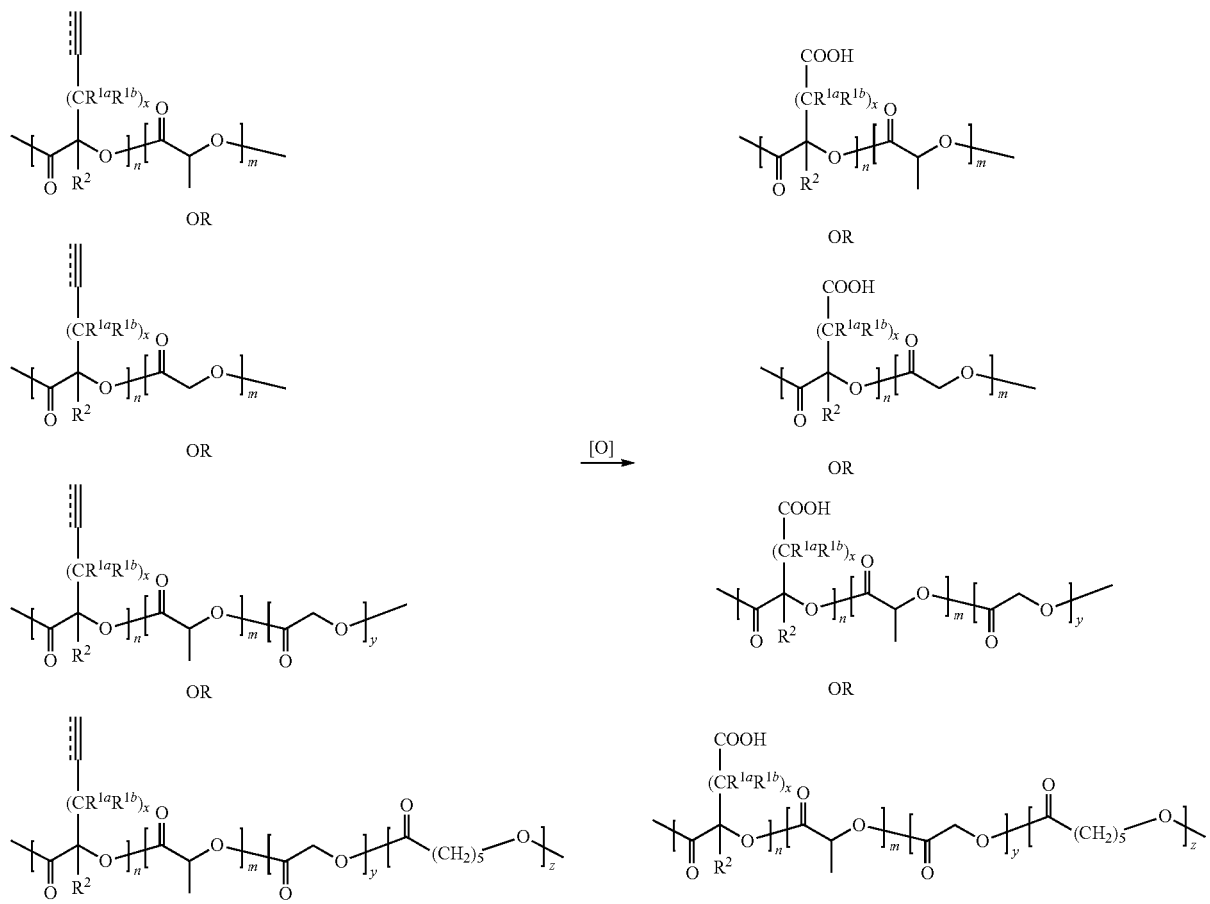

The following exemplary procedure can be used to oxidize the unsaturated polymer and introduce the carboxylic acid functional group. The unsaturated polymer can be dissolved in a suitable solvent, such as acetone. This solution can then be placed in an ice bath. An acid, such as acetic acid, can be added, for example in a 1:8 ratio relative to the total volume. That is, for example, 5 mL of acetic acid can be added to a 30 mL solution of the unsaturated polymer. A cation sequestering agent can also be used, particularly if the oxidizing agent is a salt, such as $KMnO_4$. Various crown ethers can be used, such as 18-crown-6-ether. An oxidizing agent, such as $KMnO_4$, can be added to this solution. The resulting solution can then be stirred for 1-3 hours at an ice bath temperature followed by further stirring overnight, or as much as 18-24 hours. A solvent such as ethyl acetate can then be added along with water. A reagent such as sodium hydrogensulfite can be added until the peracid byproduct is removed.

After removing the peracid byproduct, the pH of the reaction solution can be adjusted with an acid, such as 1N HCl. The organic layer can then be extracted, and subsequently washed with an acidic solution such as 1N HCl. After the organic layer is collected, the solvents can be evaporated off, and the crude polymer product can be collected. The copolymer product can be washed with solvents such as water and methanol to remove byproducts. The copolymer product can then be collected again and re-precipitated with an appropriate solvent, such as THF, as desired to achieve a copolymer of a targeted purity.

Any of the aforementioned copolymers can be used to form the microparticle of the invention, if a microparticle is desired for use. The microparticles can be prepared from the copolymers of the invention using known techniques, such as emulsion or double-emulsions processes, among other processes.

The microparticles of the invention can comprises one or more bioactive agents. The bioactive agent can be present in the microparticle in any suitable amount. For example, the bioactive agent can be present in an amount ranging from 1% to 80% by weight of the implant device, for example, 5%, 10%, 15%, 20%, 30%, 40%, 45%, 50%, 55%, 60%, 70%, or 80%.

The polymers of the invention can also be used to prepare polymer micelles. For example, a low MW PEG-polyester block copolymer that also includes the copolymer of the invention can be used to prepare polymeric micelles. In addition, dosage forms comprising the polymers of the invention alone or using blends of the polymers with one or more additional biodegradable polymers or biocompatible polymers can be used.

The polymers of the invention can also be used in films, coatings, on surfaces, including films and/or surface coatings with or without added bioactive agent. Graft copolymers can also be prepared using the polymers of the invention, for example, through attachment at the carboxylic acid group of the polymer. Similarly, the carboxylic acid group of the disclosed polymer can be used as a covalent or non-covalent attachment point for another complementary or reactive polymer, for example, to cross-link the polymer of the invention with another polymer. In addition, the carboxylic acid group can also serve as an attachment point for one or more bioactive agents or drugs, which can be the same or different when multiple bioactive agents or drugs are present. A prodrug, therefore, can be prepared from the polymers of the invention.

Examples of bioactive agents that can be incorporated into microparticles, dosages, or compositions of the invention include generally any bioactive agent. Examples include without limitation small molecules, peptides, proteins such as hormones, enzymes, antibodies, receptor binding proteins, antibody fragments, antibody conjugates, nucleic acids such as aptamers, iRNA, siRNA, microRNA, DNA, RNA, antisense nucleic acid or the like, antisense nucleic acid analogs or the like, VEGF inhibitors, macrocyclic lactones, dopamine agonists, dopamine antagonists, low-molecular weight compounds, high-molecular-weight compounds, or conjugated bioactive agents.

Other bioactive agents can include anabolic agents, antacids, anti-asthmatic agents, anti-cholesterolemic and anti-lipid agents, anti-coagulants, anti-convulsants, anti-diarrheals, anti-emetics, anti-infective agents including antibacterial and antimicrobial agents, anti-inflammatory agents, anti-manic agents, antimetabolite agents, anti-nauseants, anti-neoplastic agents, anti-obesity agents, antipsychotics, anti-pyretic and analgesic agents, anti-spasmodic agents, anti-thrombotic agents, anti-tussive agents, anti-uricemic agents, anti-anginal agents, antihistamines, appetite suppressants, biologicals, cerebral dilators, coronary dilators, bronchiodilators, cytotoxic agents, decongestants, diuretics, diagnostic agents, erythropoietic agents, expectorants, gastrointestinal sedatives, hyperglycemic agents, hypnotics, hypoglycemic agents, immunomodulating agents, ion exchange resins, laxatives, mineral supplements, mucolytic agents, neuromuscular drugs, peripheral vasodilators, psychotropics, sedatives, stimulants, thyroid and anti-thyroid agents, tissue growth agents, uterine relaxants, vitamins, or antigenic materials.

Still other bioactive agents include androgen inhibitors, polysaccharides, growth factors, hormones, anti-angiogenesis factors, dextromethorphan, dextromethorphan hydrobromide, noscapine, carbetapentane citrate, chlophedianol hydrochloride, chlorpheniramine maleate, phenindamine tartrate, pyrilamine maleate, doxylamine succinate, phenyltoloxamine citrate, phenylephrine hydrochloride, phenylpropanolamine hydrochloride, pseudoephedrine hydrochloride, ephedrine, codeine phosphate, codeine sulfate morphine, mineral supplements, cholestryramine, N-acetylprocainamide, acetaminophen, aspirin, ibuprofen, phenyl propanolamine hydrochloride, caffeine, guaifenesin, aluminum hydroxide, magnesium hydroxide, peptides, polypeptides, proteins, amino acids, hormones, interferons, cytokines, and vaccines.

Representative drugs that can be used as bioactive agents include, but are not limited to, peptide drugs, protein drugs, therapeutic antibodies, anticalins, desensitizing materials, antigens, anti-infective agents such as antibiotics, antimicrobial agents, antiviral, antibacterial, antiparasitic, antifungal substances and combination thereof, antiallergenics, androgenic steroids, decongestants, hypnotics, steroidal anti-inflammatory agents, anti-cholinergics, sympathomimetics, sedatives, miotics, psychic energizers, tranquilizers, vaccines, estrogens, progestational agents, humoral agents, prostaglandins, analgesics, antispasmodics, antimalarials, antihistamines, cardioactive agents, anti-inflammatory agents, nonsteroidal anti-inflammatory agents, antiparkinsonian agents, antihypertensive agents, β-adrenergic blocking agents, nutritional agents, anti-TNF agents and the benzophenanthridine alkaloids. The agent can further be a substance capable of acting as a stimulant, sedative, hypnotic, analgesic, anticonvulsant, and the like.

Other bioactive agents include but are not limited to analgesics such as acetaminophen, acetylsalicylic acid, and the like; anesthetics such as lidocaine, xylocaine, and the like; anorexics such as dexadrine, phendimetrazine tartrate, and the like; antiarthritics such as methylprednisolone, ibuprofen, and the like; antiasthmatics such as terbutaline sulfate, theophylline, ephedrine, and the like; antibiotics such as sulfisoxazole, penicillin G, ampicillin, cephalosporins, amikacin, gentamicin, tetracyclines, chloramphenicol, erythromycin, clindamycin, isoniazid, rifampin, and the like; antifungals such as amphotericin B, nystatin, ketoconazole, and the like; antivirals such as acyclovir, amantadine, and the like; anticancer agents such as cyclophosphamide, methotrexate, etretinate, and the like; anticoagulants such as heparin, warfarin, and the like; anticonvulsants such as phenytoin sodium, diazepam, and the like; antidepressants such as isocarboxazid, amoxapine, and the like; antihistamines such as diphenhydramine HCl, chlorpheniramine maleate, and the like; antipsychotics such as clozapine, haloperidol, carbamazepine, gabapentin, topimarate, bupropion, sertraline, alprazolam, buspirone, risperidone, aripiprazole, olanzapine, quetiapine, ziprasidone, iloperidone, and the like; hormones such as insulin, progestins, estrogens, corticoids, glucocorticoids, androgens, and the like; tranquilizers such as thorazine, diazepam, chlorpromazine HCl, reserpine, chlordiazepoxide HCl, and the like; antispasmodics such as belladonna alkaloids, dicyclomine hydrochloride, and the like; vitamins and minerals such as essential amino acids, calcium, iron, potassium, zinc, vitamin $B_{12}$, and the like; cardiovascular agents such as prazosin HCl, nitroglycerin, propranolol HCl, hydralazine HCl, pancrelipase, succinic acid dehydrogenase, and the like; peptides and proteins such as LHRH, somatostatin, calcitonin, growth hormone, glucagon-like peptides, growth releasing factor, angiotensin, FSH, EGF, bone morphogenic protein (BMP), erythropoeitin (EPO), interferon, interleukin, collagen, fibrinogen, insulin, Factor VIII, Factor IX, Enbrel®, Rituxan®, Herceptin®, alpha-glucosidase, Cerazyme/Ceredose®, vasopressin, ACTH, human serum albumin, gamma globulin, structural proteins, blood product proteins, complex proteins, enzymes, antibodies, monoclonal antibodies, and the like; prostaglandins; nucleic acids; carbohydrates; fats; narcotics such as morphine, codeine, and the like, psychotherapeutics; anti-malarials, L-dopa, diuretics such as furosemide, spironolactone, and the like; antiulcer drugs such as rantidine HCl, cimetidine HCl, and the like.

The bioactive agent can also be an immunomodulator, including, for example, cytokines, interleukins, interferon, colony stimulating factor, tumor necrosis factor, and the like; allergens such as cat dander, birch pollen, house dust mite, grass pollen, and the like; antigens of bacterial organisms such as *Streptococcus pneumoniae, Haemophilus influenzae, Staphylococcus aureus, Streptococcus pyrogenes, Corynebacterium diphteriae, Listeria monocytogenes, Bacillus anthracis, Clostridium tetani, Clostridium botulinum, Clostridium perfringens. Neisseria meningitides, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptspirosis interrogans, Borrelia burgddorferi, Campylobacter jejuni*, and the like; antigens of such viruses as smallpox, influenza A and B, respiratory synctial, parainfluenza, measles, HIV, SARS, varicella-zoster, herpes simplex 1 and 2, cytomeglavirus, Epstein-Barr, rotavirus, rhinovirus, adenovirus, papillomavirus, poliovirus, mumps, rabies, rubella, coxsackieviruses, equine encephalitis, Japanese encephalitis, yellow fever, Rift Valley fever, lymphocytic choriomeningitis, hepatitis B, and the like; antigens of such fungal, protozoan, and parasitic organisms such as *Cryptococcuc neoformans, Histoplasma capsulatum, Candida albicans, Candida tropicalis, Nocardia asteroids, Rickettsia ricketsii, Rickettsia typhi, Mycoplasma pneumoniae, Chlamyda psittaci, Chlamydia trachomatis, Plasmodium falciparum, Trypanasoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

In a further specific aspect, the bioactive agent comprises an antibiotic. The antibiotic can be, for example, one or more of Amikacin, Gentamicin, Kanamycin, Neomycin, Netilmicin, Streptomycin, Tobramycin, Paromomycin, Ansamycins, Geldanamycin, Herbimycin, Carbacephem, Loracarbef, Carbapenems, Ertapenem, Doripenem, Imipenem/Cilastatin, Meropenem, Cephalosporins (First generation), Cefadroxil, Cefazolin, Cefalotin or Cefalothin, Cefalexin, Cephalosporins (Second generation), Cefaclor, Cefamandole, Cefoxitin, Cefprozil, Cefuroxime, Cephalosporins (Third generation), Cefixime, Cefdinir, Cefditoren, Cefoperazone, Cefotaxime, Cefpodoxime, Ceftazidime, Ceftibuten, Ceftizoxime, Ceftriaxone, Cephalosporins (Fourth generation), Cefepime, Cephalosporins (Fifth generation), Ceftobiprole, Glycopeptides, Teicoplanin, Vancomycin, Macrolides, Azithromycin, Clarithromycin, Dirithromycin, Erythromycin, Roxithromycin, Troleandomycin, Telithromycin, Spectinomycin, Monobactams, Aztreonam, Penicillins, Amoxicillin, Ampicillin, Azlocillin, Carbenicillin, Cloxacillin, Dicloxacillin, Flucloxacillin, Mezlocillin, Meticillin, Nafcillin, Oxacillin, Penicillin, Piperacillin, Ticarcillin, Polypeptides, Bacitracin, Colistin, Polymyxin B, Quinolones, Ciprofloxacin, Enoxacin, Gatifloxacin, Levofloxacin, Lomefloxacin, Moxifloxacin, Norfloxacin, Ofloxacin, Trovafloxacin, Sulfonamides, Mafenide, Prontosil (archaic), Sulfacetamide, Sulfamethizole, Sulfanilimide (archaic), Sulfasalazine, Sulfisoxazole, Trimethoprim, Trimethoprim-Sulfamethoxazole (Co-trimoxazole) (TMP-SMX), Tetracyclines, including Demeclocycline, Doxycycline, Minocycline, Oxytetracycline, Tetracycline, and others; Arsphenamine, Chloramphenicol, Clindamycin, Lincomycin, Ethambutol, Fosfomycin, Fusidic acid, Furazolidone, Isoniazid, Linezolid, Metronidazole, Mupirocin, Nitrofurantoin, Platensimycin, Pyrazinamide, Quinupristin/Dalfopristin, Rifampicin (Rifampin in U.S.), Tinidazole, Ropinerole, Ivermectin, Moxidectin, Afamelanotide, Cilengitide, or a combination thereof. In one aspect, the bioactive agent can be a combination of Rifampicin (Rifampin in U.S.) and Minocycline.

The compositions or microparticles of the invention can be used as delivery vehicles to delivery the bioactive agent to a subject. The compositions or microparticles of the invention can be delivered to a subject to effectively deliver the bioactive agent to the subject. The subject can be a vertebrate, such as a mammal, a fish, a bird, a reptile, or an amphibian. The subject of the herein disclosed methods can be, for example, a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. Dosages and particular formulations can be determined by one of skill in the pharmaceutical arts and will vary widely depending on the indication being treated.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Prophetic

An α-hydroxyacid, 2-hydroxy-4-pentenoic acid (50 grams), is polymerized in bulk under high vacuum (~0.02 torr) with sulfuric acid 150 μl (0.95%, mole) as the polymerization catalyst at 120° C. for two hours. Zinc oxide, ZnO, (1 gram) is added as the transesterification catalyst, and the desired monomer is distilled off under high vacuum (~0.02 torr) and high temperature (230° C. to 240° C.) and collected on a cold-trap (on dry ice). Optionally, the collected monomer is purified by recrystallization, for example by dissolving into warm diethyl ether then cooling overnight on dry ice to recrystalize the monomer).

Example 2

To a dried flask were added diallyl lactide 0.20 grams (1.02 mmole) and lactide 1.30 gram (9.03 mmole) under nitrogen atmosphere. The flask was immersed in an oil bath heated at 130° C. After the solid melted, methyl glycolate 15.4 μl (0.20 mmole) and 43.8 μl of a toluene solution of 0.247 M tin 2-ethylhexanoate (containing 0.0108 mmole of tin 2-ethylhexanoate) were added. The liquid was stirred at 130° C. for 4 hours. After the liquid was cooled to room temperature, the liquid was dissolved in chloroform and precipitated into cold methanol. The obtained precipitate was collected and dried under vacuum at 45° C.-50° C. overnight. 1.10 grams of polymer was obtained, yield: 73.3%. $^1$H NMR (in CDCl$_3$, 300 MHz): 5.7 ppm-5.9 ppm (b, CH$_2$=CH—), 5.1 ppm-5.3 ppm (b, CH$_2$=CH—, O=C—CH—O—), 3.75 ppm (b, due to initiator methyl glycolate, CH$_3$O—C=O), 2.6 ppm-2.8 ppm (b, CH$_2$=CH—CH$_2$—), 1.4 ppm-1.7 ppm (b, CH$_3$—).

The molecular weight determined by NMR was 13,400 Daltons. The copolymer contains 10% allyl lactide units and 90% lactide units. Compared with the NMR spectrum of diallyl lactide, the polymer peaks at 5.7 ppm and 2.7 ppm are broad, whereas the diallyl lactide monomer peaks are sharp. The monomer peaks at 4.9 ppm and 5.1 ppm (isomers) shift to 5.2 ppm upon polymerization.

Various modifications and variations can be made to the compounds, composites, kits, articles, devices, compositions, and methods described herein. Other aspects of the compounds, composites, kits, articles, devices, compositions, and methods described herein will be apparent from consideration of the specification and practice of the compounds, composites, kits, articles, devices, compositions, and methods disclosed herein. It is intended that the specification and examples be considered as exemplary.

What is claimed is:

1. A copolymer having the formula:

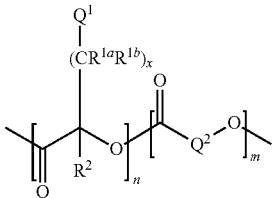

wherein n and m are each independent integers ranging from 1 to 10,000;
wherein x is an integer ranging from 0 to 12;
wherein each $R^{1a}$ and each $R^{1b}$, when present, is independently hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl;
wherein $R^2$ is hydrogen, hydroxy, amino, thio, halogen, substituted or unsubstituted $C_1$-$C_6$ alkyl, substituted or unsubstituted $C_1$-$C_6$ alkoxy, substituted or unsubstituted $C_1$-$C_6$ alkylthio, substituted or unsubstituted $C_1$-$C_6$ alkylamino, or substituted or unsubstituted $C_1$-$C_6$ hydroxyalkyl;
wherein $Q^1$ is —COOH or

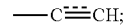

and
wherein $Q^2$ is —[(CH)CH$_3$]—, —(CH$_2$)—, or —[(CH$_2$)$_5$]—.

2. The copolymer of claim 1, wherein x is 1.
3. The copolymer of claim 1, wherein x is 2.
4. The copolymer of claim 1, wherein $R^2$ is hydrogen.
5. The copolymer of claim 1, wherein $R^{1a}$ is hydrogen.
6. The copolymer of claim 1, wherein $R^{1b}$ is hydrogen.
7. A microparticle comprising a matrix formed from the copolymer of claim 1.
8. The microparticle of claim 7, further comprising a bioactive agent encapsulated in the matrix.
9. A polymer micelle comprising the copolymer of claim 1.
10. The polymer micelle of claim 8, wherein the copolymer further comprises one or more blocks of poly(ethylene glycol) (PEG), polyvinylpyrrolidone (PVP), or a combination thereof.

* * * * *